US00PP26478P2

(12) United States Plant Patent
Heuger

(10) Patent No.: US PP26,478 P2
(45) Date of Patent: Mar. 8, 2016

(54) ***ARGYRANTHEMUM* PLANT NAMED 'SUN 300'**

(50) Latin Name: *Argyranthemum frutescens*
Varietal Denomination: SUN 300

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 14/121,236

(22) Filed: Aug. 14, 2014

(51) Int. Cl.
*A01H 5/02* (2006.01)

(52) U.S. Cl.
USPC ..... Plt./406

(58) Field of Classification Search
USPC ..... Plt./406
CPC ..... A01H 5/025; A01H 5/02
See application file for complete search history.

*Primary Examiner* — Kent L Bell
(74) *Attorney, Agent, or Firm* — C. A. Whealy

(57) ABSTRACT

A new and distinct cultivar of *Argyranthemum* plant named 'SUN 300', characterized by its compact and uniformly mounded plant habit; freely branching habit; freely flowering habit; single-type inflorescences with light yellow-colored ray florets; and good garden performance.

2 Drawing Sheets

Botanical designation: *Argyranthemum frutescens.*
Cultivar denomination: 'SUN 300'.

BACKGROUND OF THE INVENTION

The present invention relates to a new and distinct cultivar of *Argyranthemum* plant, botanically known as *Argyranthemum frutescens* and hereinafter referred to by the cultivar name 'SUN 300'.

The objective of the breeding program is to create new compact *Argyranthemum* plants with attractive ray and disc floret colors and good garden performance and pest resistance.

The new *Argyranthemum* plant originated from a cross-pollination made by the Inventor in July, 2012 in Glandorf, Germany of two unnamed seedling selections of *Argyranthemum frutescens*, not patented. The new *Argyranthemum* plant was discovered and selected by the Inventor as a single flowering plant from within the progeny of the stated cross-pollination in a controlled greenhouse environment in Glandorf, Germany in June, 2013.

Asexual reproduction of the new *Argyranthemum* plant by vegetative tip cuttings was first conducted in Glandorf, Germany in August, 2013. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of the new *Argyranthemum* plant. These characteristics in combination distinguish 'SUN 300' as a new and distinct *Argyranthemum* plant:

1. Compact and uniformly mounded plant habit.
2. Freely branching habit.
3. Freely flowering habit.
4. Single-type inflorescences with light yellow-colored ray florets.
5. Good garden performance.

Plants of the new *Argyranthemum* differ from plants of the parent selections primarily in plant size and uniformity.

Plants of the new *Argyranthemum* can be compared to plants of *Argyranthemum frutescens* 'SUN 10', disclosed in U.S. Plant Pat. No. 19,333. In side-by-side comparisons conducted in Glandorf, Germany, plants of the new *Argyranthemum* differed from plants of 'SUN 10' primarily in ray floret color.

BRIEF DESCRIPTION OF THE PHOTOGRAPHS

The accompanying photographs illustrate the overall appearance of the new *Argyranthemum* showing the colors as true as it is reasonably possible to obtain in colored reproductions of this type. Colors in the photographs may differ slightly from the color values cited in the detailed botanical description which accurately describe the colors of the new *Argyranthemum* plant.

The photograph on the first sheet comprises a side perspective view of a typical flowering plant of 'SUN 300' grown in a container.

The photograph on the second sheet is a close-up view of typical inflorescences of 'SUN 300'.

DETAILED BOTANICAL DESCRIPTION

The aforementioned photographs and following observations and measurements describe plants grown during the winter and early spring in 10.5-cm containers in a glass-covered greenhouse in Glandorf, Germany under cultural practices typical of commercial potted *Argyranthemum* production. During the production of the plants, day temperatures ranged from 14° C. to 28° C., night temperatures ranged from 10° C. to 18° C. and light levels ranged from 25 klux to 90 klux. Plants were pinched one time three to four weeks after planting and were 2.5 months old when the photographs and description were taken. In the following description, color references are made to The Royal Horticultural Society Colour Chart, 2001 Edition, except where general terms of ordinary dictionary significance are used.

Botanical classification: *Argyranthemum frutescens* 'SUN 300'.

Parentage:

*Female, or seed, parent*.—Unnamed seedling selection of *Argyranthemum frutescens*, not patented.

*Male, or pollen, parent*.—Unnamed seedling selection of *Argyranthemum frutescens*, not patented.

Propagation:

*Type*.—Terminal cuttings.

*Time to initiate roots, summer*.—About 8 to 10 days at temperatures about 18° C. to 24° C.

*Time to initiate roots, winter*.—About 10 to 15 days at temperatures about 14° C. to 18° C.

*Time to produce a rooted young plant, summer*.—About 14 to 16 days at temperatures about 18° C. to 24° C.

*Time to produce a rooted young plant, winter*.—About 16 to 20 days at temperatures about 14° C. to 18° C.

*Root description*.—Fine to medium in thickness, fibrous; white in color.

*Rooting habit*.—Moderate branching; medium density.

Plant description:

*Plant and growth habit*.—Herbaceous; compact and uniform mounding plant habit; upright to broadly spreading form; moderately vigorous growth habit.

*Branching habit*.—Freely branching growth habit with about seven lateral branches developing per plant; dense and bushy plant form; pinching enhances lateral branch development.

*Plant height*.—About 15.3 cm.

*Plant width*.—About 26.8 cm.

*Lateral branches*.—Length: About 8.1 cm. Diameter: About 4 mm. Internode length: About 8 mm. Strength: Strong; young stems, flexible. Texture: Smooth, sparsely pubescent. Color: Close to 145B.

Leaf description:

*Arrangement*.—Alternate, simple; sessile.

*Length*.—About 8.6 cm.

*Width*.—About 5.1 cm.

*Shape*.—Pinnatisect; in outline, obovate.

*Apex*.—Broadly acute.

*Base*.—Cuneate.

*Margin*.—Pinnatifid; laciniate.

*Sinuses*.—Parallel to slightly convergent.

*Texture, upper and lower surfaces*.—Smooth, glabrous; slightly rough; venation on lower surface, sparsely pubescent.

*Venation*.—Pinnate.

*Color*.—Developing leaves, upper surface: Close to 137B. Developing leaves, lower surface: Close to 143A. Fully expanded leaves, upper surface: Close to N137B to N137C; venation, close to 138A to 138B. Fully expanded leaves, lower surface: Close to 137C; venation, close to 143B.

Inflorescence description:

*Inflorescence form and arrangement*.—Single-type terminal and axillary inflorescences borne above and beyond the foliar plane; ray and disc florets arranged acropetally on a receptacle; inflorescences face mostly upright to slightly outwardly.

*Flowering habit*.—Freely flowering habit with about 300 inflorescences develop per plant.

*Flowering season*.—Plants flower from spring to late summer in Germany; flowering continuous during this period.

*Inflorescence longevity*.—Inflorescences last about two weeks on the plant; inflorescences not persistent.

*Fragrance*.—No fragrance detected.

*Inflorescence buds*.—Height: About 9 mm. Diameter: About 8 mm. Shape: Broadly ovate. Color: Towards the base, close to 143C; mid-section, close to 199C; towards the apex, close to 4A to 4B.

*Inflorescence size*.—Diameter: About 4.4 cm. Depth (height): About 1.1 cm. Diameter of disc: About 1.2 cm. Receptacle diameter: About 4 mm. Receptacle height: About 4 mm.

*Ray florets*.—Quantity per inflorescence and arrangement: About 18 arranged in about two whorls. Length: About 2 cm. Width: About 7 mm. Shape: Obovate to oblong; slightly reflexed. Apex: Reuse to emarginate. Base: Attenuate. Margin: Entire. Texture, upper and lower surfaces: Smooth, glabrous; velvety. Color: When opening, upper surface: Close to 3C. When opening, lower surface: Close to 3D. Fully opened, upper surface: Close to between 1D and 2D. Fully opened, lower surface: Close to 150D.

*Disc florets*.—Quantity per inflorescence and arrangement: About 160 massed at center of receptacle. Length: About 5 mm. Diameter, apex: About 2 mm. Diameter, base: About 0.75 mm. Shape: Tubular. Apex: Five-pointed; acute. Texture: Smooth, glabrous. Color, immature: Base: Close to 145B to 145C. Mid-section: Close to 145C to 145D. Apex: Close to 12A. Color, mature: Base: Close to 145B. Mid-section: Close to 145C. Apex: Close to 12A.

*Phyllaries*.—Quantity per inflorescence and arrangement: About 26 arranged in two whorls. Length: About 6 mm. Width: About 3 mm. Shape: Ovate. Apex: Praemorse. Base: Broadly cuneate. Margin: Entire. Texture, upper and lower surfaces: Smooth, glabrous; margins, papery. Color, upper surface: Close to 144B; margins, close to 199D. Color, lower surface: Close to 144A; margins, close to 199D.

*Peduncles*.—Length, terminal peduncle: About 3.8 cm. Length, fourth peduncle: About 3.5 cm. Diameter: About 1.5 mm. Angle: Mostly erect to about 40° from vertical. Strength: Strong, flexible. Texture: Smooth, glabrous. Color: Close to 143B.

*Reproductive organs*.—Androecium: Present on disc florets only. Filament length: About 1.5 mm. Anther length: About 1 mm. Anther shape: Lanceolate. Anther color: Close to 12A. Pollen amount: Abundant. Pollen color: Close to 14A to 14B. Gynoecium: Present on both ray and disc florets. Pistil length: About 4 mm. Stigma shape: Decurrent. Stigma color: Close to 12A. Style length: About 3 mm. Style color: Close to 145A. Ovary color: Close to 145C to 145D.

*Seeds and fruits*.—Seed and fruit production has not been observed on plants of the new *Argyranthemum*.

Disease & pest resistance: Plants of the new *Argyranthemum* have not been shown to be resistant to pathogens and pests common to *Argyranthemum* plants.

Garden performance: Plants of the new *Argyranthemum* have been observed to have good garden performance and to tolerate rain, wind, high temperatures about 40° C. and to be hardy to USDA Hardiness Zone 9.

It is claimed:

1. A new and distinct *Argyranthemum* plant named 'SUN 300' as illustrated and described.

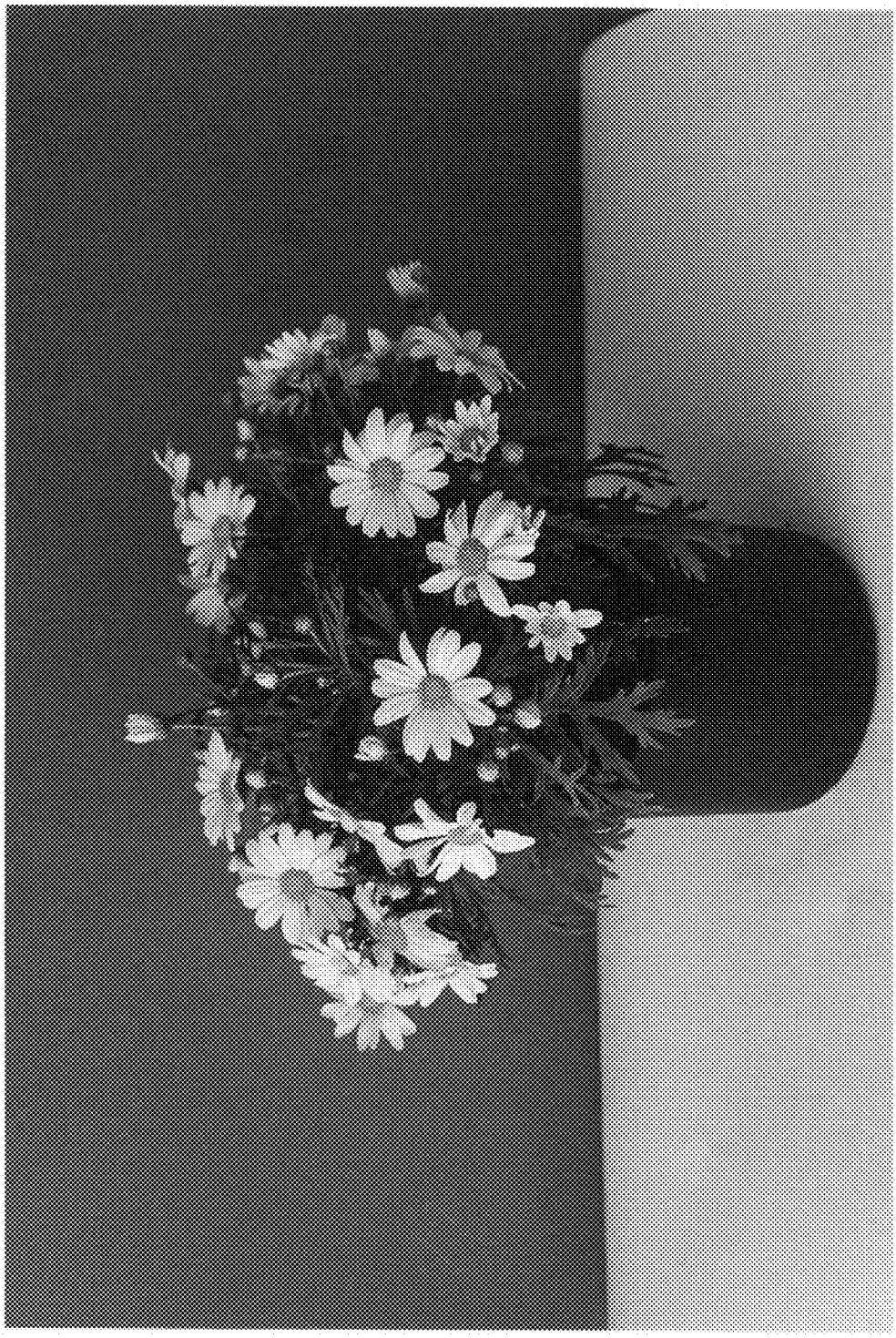

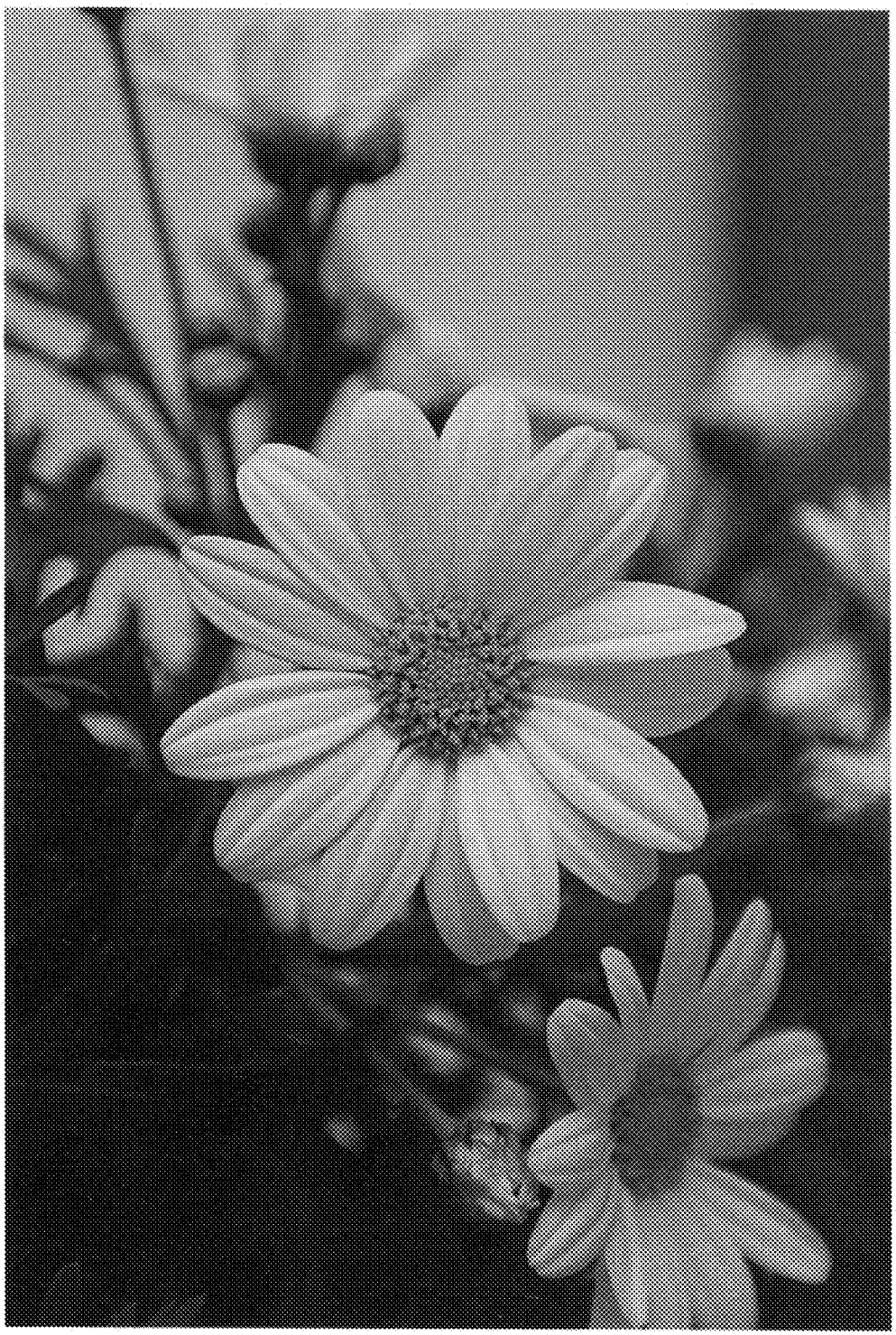

* * * * *